US006506395B2

(12) United States Patent
Lillig

(10) Patent No.: US 6,506,395 B2
(45) Date of Patent: Jan. 14, 2003

(54) METHOD OF ATTRACTING WILDLIFE USING HEDGE APPLE EXTRACT

(76) Inventor: James Lillig, 1615 E. 173rd St., Belton, MO (US) 64102

( * ) Notice: Subject to any disclaimer, the term of this patent is extended or adjusted under 35 U.S.C. 154(b) by 0 days.

(21) Appl. No.: 09/809,815

(22) Filed: Mar. 16, 2001

(65) Prior Publication Data

US 2002/0132020 A1 Sep. 19, 2002

(51) Int. Cl.7 .................................................. A61K 35/78
(52) U.S. Cl. .................... 424/405; 424/725; 424/777
(58) Field of Search ................................. 424/405, 725, 424/777

(56) References Cited

U.S. PATENT DOCUMENTS

| 5,607,673 A | 3/1997 | Bashengezi |
| 5,901,490 A | 5/1999 | Lush |
| 5,916,552 A | 6/1999 | Perry |
| 6,030,608 A | 2/2000 | Hoyes et al. |
| 6,165,570 A | 12/2000 | Shannon |
| 6,171,593 B1 | 1/2001 | Williams |

OTHER PUBLICATIONS

Bryant et al. Prairie Naturalist (1996), vol. 28, No. 3, pp. 125–140.*
Hedgeapple Web site; hedgeapple.com; visited Feb. 15, 2001.
Osage Orange Web site; www.gpnc.org; visited Feb. 15, 2001.
Iowa State University Web site; www.ent.iastate.edu; visited Feb. 15, 2001.

* cited by examiner

Primary Examiner—Leon B. Lankford, Jr.
Assistant Examiner—Susan D. Coe
(74) Attorney, Agent, or Firm—Stinson Morrison Hecker LLP

(57) ABSTRACT

The present invention is directed to a wildlife attractant comprised of an extract from the fruit of the hedge apple tree and methods for using the attractant to attract deer and cover the scent of a human user.

12 Claims, No Drawings

METHOD OF ATTRACTING WILDLIFE USING HEDGE APPLE EXTRACT

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The present invention relates to a method and compound for attracting wildlife, more specifically to a method of using the extract of the hedge apple fruit as a deer attractant and/or cover scent.

2. Description of Related Art

Hunters, wildlife enthusiasts and wildlife photographers all have an interest in attracting wildlife, such as deer. Deer rely heavily on their sense of smell to react with their surrounding environment, including to sense danger, interact with other deer and find food. Scents that are not a natural part of the environment will often function as a warning to deer, which may result in the deer being spooked and running from the unnatural scent. As a result, persons interested in attracting deer must mask their scent to prevent spooking the deer. Because deer rely so heavily on their sense of smell, many known deer attractants use various scents to attract deer and cover the scent of the human wishing to attract the deer.

For example, because deer are known to be attracted by certain scents secreted by other deer, many known attractants contain materials obtained from deer. Deer urine produced during the rutting season is known to contain pheromones that attract other deer. As a result, various deer attractants contain some form of deer urine. Other attractants use hair taken from the tarsal gland region of a deer. Although such deer attractants have had success in luring deer, various problems exist with such attractants, including a smell that is offensive to the human user and a limited shelf life. In addition, the deer products contained in such deer attractants, such as pheromone-rich urine, occur in the natural environment only during certain seasons. The use of such scent outside of the natural season would be out of place to a deer, and likely would spook, rather than attract, the deer. Similarly, certain non-natural chemicals used in, or added to, a deer attractant would be out of place in the natural environment, and likely would spook a deer.

In many instances, the deer's natural environment contains hedge apple trees. The hedge apple fruit is eaten by deer, particularly during the winter months. Although hedge apples are native to the South Central United States, they are now found throughout the Great Plains and other areas of the United States. The hedge apple tree, commonly referred to as osage orange trees, bois d'arc or bowwood trees, belongs to the family Moraceae and varieties are generally classified as *Maclura pomifera* or *Maclura aurantiaca*. The fruit of the hedge apple tree, which is called a hedge apple, is a round rough skinned fruit inedible by humans. Hedge apple fruit is thought to be effective in repelling insects, and extract from the fruit has been shown to repel cockroaches. It is suspected that 2,3,4,5-tetrahydroxystilbene is the chemical in the hedge apple fruit that is responsible for repelling insects.

SUMMARY OF THE INVENTION

The present invention is directed to a wildlife attractant comprising an extract from the fruit of the hedge apple tree and a method for using the extract to attract wildlife, preferably deer or other game, and to cover the scent of the human user. The wildlife attractant of the present invention does not require use of natural animal products, for example urine or hair, that have been used in prior game attractants. However, the hedge apple extract of the present invention may be used to attract wildlife, preferably deer or other wild game, and to cover the scent of a human in the same manner as conventional game attractants.

The wildlife attractant of the present invention comprises an extract from the hedge apple fruit. The extract may be produced using conventional extraction and distillation techniques. In a preferred embodiment the hedge apple fruit is ground into small pieces and water is added to create a pulp. The water and the volatile liquids, which contain the components of the hedge apple fruit that produce the hedge apple scent, are then extracted from the pulp by standard extraction and distillation techniques. For example, the pulp may be boiled under pressure to release the water and volatile liquids which are condensed and collected. Preferably a preservative is added to the extract. Optionally a colorant may be added as well.

The attractant of the present invention can be readily made from hedge apple fruit, which is inexpensive and widely available. Further, the method of extracting the wildlife attractant from the hedge apple fruit is simple, cost effective and can be carried out using standard distilling equipment. In addition, the extract of the present invention eliminates the need to obtain, handle and process animal urine or hair. Also, because the extract of the present invention does not contain animal urine, it does not possess the offensive smells associated with such products and it may be more desirable to human users.

DETAILED DESCRIPTION OF PREFERRED EMBODIMENT

The wildlife attractant of the present invention is comprised of an extract from the fruit of the hedge apple tree. Alternatively, the wildlife attractant of the present invention may comprise any natural or synthetic compound that possesses the scent of hedge apple fruit. The extract preferably comprises the chemical compound or compounds within the hedge apple that produce the hedge apple scent that attracts wildlife. Without wishing to be limited to any one theory, it is possible that the chemical in the hedge apple extract that is responsible for attracting deer is the 2,3,4,5-tetrahydroxysilbene thought to be present in the hedge apple fruit.

The wildlife attractant may also contain a preservative, such as potassium sorbate, although any preservatives known in the art that do not interfere with the attractant properties of the extract can be used. The attractant may optionally contain a colorant to enhance the appearance. A suitable colorant can easily be selected by one of ordinary skill in the art. Preferably the colorant is green to simulate the color of the hedge apple fruit.

The attractant may be formed using standard extraction and distillation techniques, as will be readily apparent to those in the art. In a preferred embodiment, the hedge apple fruit is ground, or pulverized, into small particles using a conventional blender, mill or other grinding apparatus known in the art. A solvent, preferably water, is then added and mixed with the ground hedge apple in a sufficient amount to create a pulp that is preferably the consistency of paste.

The solvent and the components of the fruit carrying the hedge apple scent are extracted from the pulp using standard extraction and/or distillation techniques. In a preferred embodiment, the pulp is boiled, preferably under pressure, to release and evaporate the solvent and other volatile liquids in the pulp, which solvent and/or volatile liquids contain the components of the hedge apple fruit that carry the hedge apple scent. The solvent and volatile liquids containing the hedge apple scent are then condensed and collected. The extract may be further concentrated using standard distillation techniques. Preferably a preservative is added to the extract, more preferably potassium sorbate, although any other preservative known in the art that will not materially affect the nature or volatility of the scent contained in the extract may be used. Further, a colorant, preferably a green colorant, may be added to enhance the appearance of the extract. The colorant may be selected and incorporated by any method known in the art. The extract may then be poured into bottles or jars, preferably tinted bottles or jars, for distribution to users. The bottles or jars may be sealed by any method known in the art, such as by standard home canning techniques.

The wildlife attractant of the present invention may be used to attract wildlife or to cover the scent of a human wishing to attract wildlife. Preferable the attractant is a deer attractant, used to attract deer. To attract deer to a desired location, the deer attractant is dispensed near the desired location. Preferably, the deer attractant is applied to the bushes, trees and ground in the surrounding area, more preferably to the bushes, trees and ground up-wind of the desired location. Alternatively, the attractant of the present invention may be dispensed by spraying it into the air or using any of several scent dispensers known in the art. By way of example only, suitable deer attractant scent dispensers include a pad soaked with the attractant, a gelatin containing the attractant, or a receptacle containing the attractant and a wick comprised of cotton or other suitable wicking material. To cover the scent of a human user, the deer attractant may be applied to the skin or clothing of the user, or to the area surrounding the user.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and sub-combinations are of utility and may be employed without reference to other features and sub-combinations. This is contemplated by and is within the scope of the claims.

What is claimed and desired to be secured by Letters Patent is as follows:

1. A method of attracting wildlife comprising:

providing a wildlife attractant comprising an extract from the fruit of a hedge apple tree, wherein said extract is present in a form and amount effective to attract wildlife; and dispensing said attractant in an area near a location at which the wildlife is desired to be attracted.

2. The method as claimed in claim 1, wherein said wildlife is a deer.

3. The method as claimed in claim 2, wherein the dispensing of the attractant comprises applying said attractant to bushes, trees and ground surrounding said location.

4. The method as claimed in claim 3, wherein the dispensing of the attractant comprises applying said attractant to bushes, trees and ground up-wind of said location.

5. The method as claimed in claim 2, wherein the dispensing of the attractant comprises spraying said attractant into the air surrounding said location.

6. The method as claimed in claim 5, wherein the dispensing of the attractant comprises spraying said attractant into the air up-wind of said location.

7. The method as claimed in claim 2, wherein the dispensing of the attractant comprises dispensing said attractant using a conventional deer scent dispensing apparatus selected from the group consisting of a pad soaked with said attractant, a gelatin containing said attractant, and a receptacle containing said attractant and a wick.

8. The method as claimed in claim 2, further comprising before the step of providing the wildlife attractant, the step of producing said attractant, wherein producing said attractant comprises the step of extracting the components of the fruit of the hedge apple tree which contain a scent of said fruit.

9. A method for covering the scent of a human in order to avoid detection by wildlife comprising:

providing a wildlife attractant comprising an extract from the fruit of a hedge apple tree, wherein said extract is present in a form and amount sufficient to mask the scent of a human user; and dispensing said attractant near the human user.

10. The method as claimed in claim 9, wherein the dispensing of the attractant comprises applying said attractant to the clothing or skin of the human user.

11. The method as claimed in claim 10, further comprising before the step of providing the wildlife attractant, the step of producing said attractant, wherein producing said attractant comprises the step of extracting the components of the fruit of the hedge apple tree which contain a scent of said fruit.

12. A method of attracting wildlife comprising:

providing a composition possessing the scent of a hedge apple; and dispensing said composition in an area near a location at which the wildlife is desired to be attracted.

* * * * *